United States Patent [19]
Henderson et al.

[11] Patent Number: 5,911,158
[45] Date of Patent: Jun. 8, 1999

[54] PIEZOELECTRIC STRAIN SENSOR ARRAY

[75] Inventors: Douglas A. Henderson, Dayton; Robert W. Gordon, Vandalia; Joseph W. Hollkamp, Fairborn, all of Ohio; Gregory S. Agnes, Christiansburg, Va.

[73] Assignee: The United States of America as represented by the Secretary of the Air Force, Washington, D.C.

[21] Appl. No.: 08/808,365

[22] Filed: Feb. 28, 1997

Related U.S. Application Data

[60] Provisional application No. 60/012,559, Feb. 29, 1996.

[51] Int. Cl.$^6$ ............................ G01H 11/08; G01N 29/12
[52] U.S. Cl. ............................... 73/583; 73/659; 702/39; 702/35; 310/336; 310/328
[58] Field of Search ........................... 73/579, 583, 659, 73/763, 767, 768, 774, 775, 777, 778, 780, 862.046, 862.07, 862.59; 310/328, 330, 331, 332, 336, 340, 365, 366, 334, 800; 364/506, 508, 550, 551.01, 576, 578; 702/33, 35, 36, 39, 56

[56] References Cited

U.S. PATENT DOCUMENTS

| | | | |
|---|---|---|---|
| 3,894,243 | 7/1975 | Edelman et al. .......................... 307/400 |
| 4,975,616 | 12/1990 | Park .......................................... 310/339 |
| 4,982,611 | 1/1991 | Lorenz et al. ......................... 73/862.04 |
| 5,191,791 | 3/1993 | Gerardi et al. .......................... 73/178 R |
| 5,195,046 | 3/1993 | Gerardi et al. ............................ 364/506 |
| 5,656,882 | 8/1997 | Lazarus et al. ............................ 310/328 |
| 5,687,462 | 11/1997 | Lazarus et al. ........................... 310/330 |

*Primary Examiner*—Hezron Williams
*Assistant Examiner*—Rose M. Miller
*Attorney, Agent, or Firm*—Fredric L. Sinder; Thomas L. Kundert

[57] ABSTRACT

An apparatus and method for determining the dynamic response of a physical structure is disclosed. A single sheet of a piezoelectric polymer film, preferably polyvinylidene fluoride, or PVDF, is coated on one side with a thin layer of conductive material to serve as a ground electrode. The other side of the sheet is coated with a thin layer or conductive material in a non-contiguous pattern of individual electrodes defining an array of discrete piezoelectric transducers. Sensor leads are connected to each individual electrode and lead to a signal processor which includes associated software for determining from the processed electrical signals relative strain amplitudes of the surface area of a physical structure onto which the sheet is attached. The resulting output can be used to record strain time histories for later processing or, more simply, to show the time-averaged, steady state strain response of a structure.

3 Claims, 1 Drawing Sheet

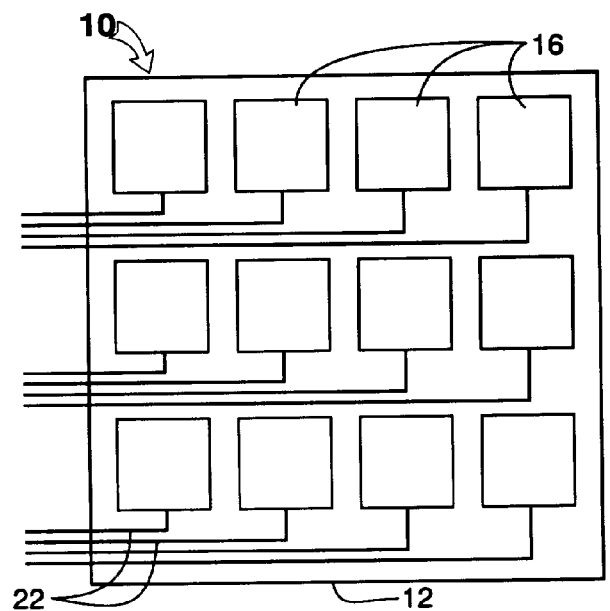
*Fig. 1*
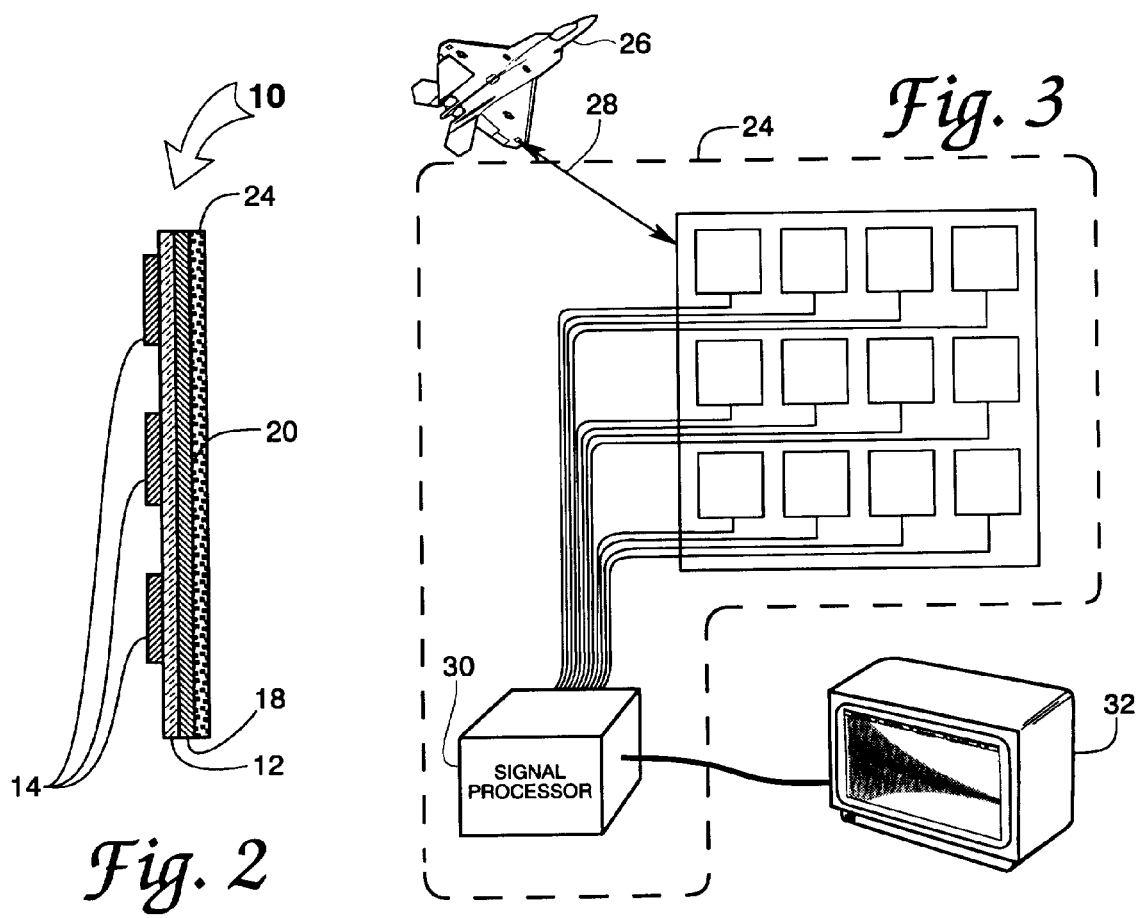
*Fig. 2*
*Fig. 3*

PIEZOELECTRIC STRAIN SENSOR ARRAY

CROSS-REFERENCE TO RELATED APPLICATIONS

This application claims priority under 35 U.S.C. § 119(e) from U.S. Provisional Application No. 60/012,559, filed Feb. 29, 1996, by applicants Douglas A. Henderson, Robert W. Gordon, Joseph J. Hollkamp and Gregory S. Agnes, entitled Piezoelectric Strain Sensor Array. The invention description contained in that provisional application is incorporated by reference into this description.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to apparatus and methods for measuring the dynamic response of physical structures, and more specifically to a system for measuring the spatial distribution of relative vibratory strain over the surface of a structure using an array of piezoelectric polymer film strain sensors coupled with a signal processor.

Knowledge of the spatial distribution of vibratory strain in a structure, such as an aircraft wing, is very useful in a design process. Areas of relatively high vibratory strain are likely locations for fatigue damage to occur. Fatigue damage can drastically reduce the service life of a structure, resulting in additional costs and downtime for repair or replacement of prematurely failed parts. Annual maintenance and repair of aircraft structures costs the U.S. Air Force hundreds of millions of dollars, making it one of the most significant post-production costs during the life cycle of aircraft. Determining the distribution of vibratory strain in these structures is an important step in diagnosing structural fatigue related problems and designing cost effective solutions. Experimental identification of these locations will permit design changes to reduce the strain or identify areas for application of damping treatments. Additionally, knowledge of strain mode shapes, the patterns of strain a structure exhibits while in resonant vibration, are extremely useful for improving mathematical design models of a structure.

No practical method exists in the prior art for measuring the absolute vibratory strain distribution over the surface of a structure. Conventional foil-type electrical resistance strain gages are capable of measuring dynamic strain at a single point on a structure. However, the cost and effort required to instrument the surface of a structure with an array of resistance strain gages in sufficient number to measure strain distribution are prohibitive.

It would be sufficient for many applications to measure the relative vibratory surface strain distribution on a structure instead of the absolute strain. Relative strain may be defined as proportional to absolute strain. Unfortunately, no practical method exists in the prior art to precisely measure relative strain distribution. Relative strain distribution can be mathematically estimated from the displacement mode shapes of a vibrating structure. However, this approach suffers from major drawbacks. First, it would be a complex and expensive task to measure the displacement mode shapes. Typically, this would require using a large number of accelerometers to obtain the dynamic displacement response of a test structure. Closely spaced measurement locations would be required to obtain smooth strain maps. Additionally, the mathematical estimation of strain shapes from displacement mode shapes can introduce significant errors. Because the mode shapes are proportional to displacement, they must be differentiated twice spatially to obtain a strain shape, adding more opportunities for computational noise and errors to enter into a final modal strain map estimate. The prior art typically uses measured displacement shapes only for updating a computerized finite element model and then obtains strain fields from the computerized model.

A more direct approach for obtaining strain shapes, or stain maps, for indicating dynamic strain distributions on structural surfaces is to use strain sensors to directly collect strain response data and use that data to identify the modal strain map. An alternative type of strain sensor from conventional electrical resistance strain gages has received much recent attention. Piezoelectric polymer films, usually made of polyvinylidene fluoride, or PVDF, have found recent use in such items as computer keyboards. See, for example, U.S. Pat. No. 4,975,616 to Park for a Piezoelectric Transducer Array. The Park patent expands on the more usual keyboard use of PVDF films as merely on-off switches.

The advantages of using PVDF film as a strain sensor are evident. They are lightweight, durable, can be shaped and stacked, have a high sensitivity to strain and can be isotropic in plane. Unfortunately, if used as a straight replacement for electrical resistance strain gages for obtaining strain maps, they suffer from many of the same deficiencies as electrical resistance strain gages.

Thus it is seen that there is a need for a successful adaptation of PVDF and other piezoelectric polymer films for use in measuring relative vibratory strain that utilizes the advantages of such films and avoids the disadvantages of other strain sensors that might be used for that purpose.

It is, therefore, a principal object of the present invention to provide a improved system for determining the dynamic response of physical structures using a piezoelectric polymer film.

It is a feature of the present invention that its incorporation of a strain sensor array onto a single sheet of piezoelectric polymer film provides a strain sensor system that is much easier, faster and less expensive to install than electrical resistance strain gages.

It is another feature of the present invention that, unlike electrical resistance strain gages, external excitation or electrical bridging is not required.

It is an advantage of the present invention that because an array of strain sensors can be produced on a single polymer sheet, a single strain sensor array replaces a large number of prior art strain sensors and the cost and effort of individually applying them.

It is another advantage of the present invention it requires no complex signal conditioning.

It is a further advantage of the present invention that its strain sensor arrays can be easily made in various sizes and smaller sizes can be easily made by simply cutting larger sizes with a scissors.

These and other objects, features and advantages of the present invention will become apparent as the description of certain representative embodiments proceeds.

SUMMARY OF THE INVENTION

In accordance with the foregoing principles and objects of the present invention, a novel system for determining the dynamic response of physical structures using a piezoelectric polymer film is described. The unique discovery of the present invention is that relatively large, easily applied, sheets of piezoelectric polymer film can be formed with an array of discrete transducer sensor areas and coupled with a signal processor to accurately measure the spatial distribution of relative vibratory strain over the surface of a structure.

Accordingly, the present invention is directed to a system for determining the dynamic response of a physical structure, comprising a sheet of piezoelectric polymer film, the sheet having a first side and a second side, a contiguous first layer of conductive film on the first side of the sheet forming a first electrode, a non-contiguous second layer of conductive film on the second side of the sheet, the non-contiguous areas of the second layer forming an array of discrete second electrodes defining a corresponding array of discrete piezoelectric transducers, and, a plurality of sensor leads, each sensor lead connected to a single corresponding second electrode, and a signal processor for receiving and processing electrical signals received from the array of discrete piezoelectric transducers, the signal processor including associated software for determining from the processed electrical signals relative strain amplitudes of the surface area of a physical structure onto which the sheet is attached. The system may further comprise an adhesive backing layer on the first electrode.

The present invention is also directed to a method for determining the dynamic response of a physical structure, comprising the steps of bonding to a surface of the physical structure a piezoelectric strain sensor array, the strain sensor array including a sheet of piezoelectric polymer film, the sheet having a first side and a second side, a contiguous first layer of conductive film on the first side of the sheet forming a first electrode, a non-contiguous second layer of conductive film on the second side of the sheet, the non-contiguous areas of the second layer forming an array of discrete second electrodes defining a corresponding array of discrete piezoelectric transducers, and a plurality of sensor leads, each sensor lead connected to a single corresponding second electrode; and, connecting the sensor leads to a signal processor for receiving and processing electrical signals received from the array of discrete piezoelectric transducers, the signal processor including associated software for determining from the processed electrical signals relative strain amplitudes of a surface area of the physical structure onto which the sheet is attached.

DESCRIPTION OF THE DRAWINGS

The present invention will be more clearly understood from a reading of the following detailed description in conjunction with the accompanying drawings wherein:

FIG. 1 is a top view of a piezoelectric strain sensor array according to the teachings of the present invention;

FIG. 2 is a side view of the piezoelectric strain sensor array of FIG. 1; and,

FIG. 3 is a diagrammatic view of a system according to the teachings of the present invention for measuring the spatial distribution of relative vibratory strain over part of the surface of an aircraft structure.

DETAILED DESCRIPTION

Referring now to FIG. 1 of the drawings, there is shown a top view of a piezoelectric strain sensor array 10 according to the teachings of the present invention. FIG. 2 is a side view of piezoelectric strain sensor array 10. Strain sensor array 10 is fabricated on a single sheet 12 of PVDF polymer film. A thin layer 14 of conductive metal is deposited on one side of sheet 12 in a non-contiguous pattern to form individual discrete electrodes 16. A contiguous, preferably continuous, layer 18 of conductive material is deposited on the other side of sheet 12 to form a ground plane electrode 20. Insulated sensor leads 22 are connected to corresponding electrodes 16. The size and shape of electrodes 16 define an array of corresponding discrete piezoelectric transducers, or strain sensors. The size, shape, number and array pattern of individual strain sensors can be chosen for a specific application. An adhesive backing 24 is attached to ground plane electrode 20 for attaching or bonding strain sensor array 10 to the surface area of a structure for which its dynamic response is to be measured.

Earlier proposed versions of strain sensor array 10 included a layer of insulated material applied to the PVDF sheet to insulate the sensor leads from the sheet. The reason for that insulation was that because the entire sheet will normally exhibit a piezoelectric effect, so that deflection of the sheet, and resulting strains, would show up as a charge on the surface areas of the sheet not covered by an electrode. Those surface charges would affect the signal voltages through the sensor leads passing over or near to those surfaces. Ktech Corporation, Albuquerque N. Mex., the North American licensee for a PVDF electrical poling process described in U.S. Pat. Nos. 4,684,337 and 4,611,260 to Bauer, which are based on French patent 82-21025 to Bauer, now supplies PVDF sheets for which piezoelectric effects do not exist across the entire sheet, but only for a preselected pattern, such as the array pattern indicated by the pattern of electrodes shown in FIG. 1. U.S. Pat. No. 5,486,320 to Bauer, also based on an earlier French patent to Bauer, describes this process. The sensor leads for such a PVDF sheet then will not be affected by strains in the sheet and the insulation is not needed.

To measure strain directly using conventional foil resistance strain gages, because such strain gages are unidirectional, they must be applied in rosette form to include orthogonal axes. However, each piezoelectric polymer film sensors, such as are used in the present invention, are bi-directional so that they effectively sum the strain in two orthogonal directions $$S_T = S_1 + S_2 \quad (1)$$

where $S_1$ is the elongation strain in the x direction and $S_2$ is the elongation strain in the y direction.

The output voltage from a piezoelectric polymer film sensor, such as a PVDF sensor, is related to the charge as follows. It can be shown that the total charge, $q_T$, is related to the elongation strain by $$q_T(t) = \int_A (e_{31}S_1 + e_{32}S_2 + e_{36}S_6 + \in_{33} E_3) dx\, dy \quad (2)$$

where A is the area of the sensor, $e_{31}$ and $e_{32}$ are the piezoelectric constants, i.e., electric charge density per applied strain in the x and y directions respectively, $S_6$ is the shear strain in the x-y plane, $E_3$ is an applied electric field in the z direction and $\in_{33}$ is the permittivity constant of the piezoelectric material in the z direction. For this application, there is no field applied ($E_3=0$), the shear strain in the x-y direction, $S_6$, is assumed to be zero and the piezoelectric material is assumed to be isotropic ($e_{31}=e_{32}$). After integrating over the area of the sensor, equation (2) reduces to $$q(t) = A e_{31}(S + S_2) \tag{3}$$

The voltage, V, is related to the charge by $$V = \frac{1}{C}q, \tag{5}$$

so equation (3) becomes $$V(t) = \frac{A e_{31}}{C}(S_1 + S_2) \tag{4}$$

where C is the capacitance between the sensor electrodes. If one assumes that all sensors are identical, then one can simplify equation (4) to $$V(t) K(S_1 + S_2) \tag{5}$$

where K is a constant. Then one can substitute equation (1) into equation (5) to obtain $$V(t) = K S_T. \tag{6}$$

Thus, the summation of planar strain is proportional to the sensor output voltage for each sensor in the array.

FIG. 3 is a diagrammatic view of a system 24 according to the teachings of the present invention for measuring the spatial distribution of relative vibratory strain over part of the surface of an aircraft 26. System 24 includes a piezoelectric strain sensor array 28 for attaching to aircraft 26. The output voltages from strain sensor array 28 attach to a signal processor 30. Signal processor 30 represents any of a variety of standalone and combinations of conventional data acquisition and processing apparatus such as will be readily apparent to those of ordinary skill in the art of the invention. For example, signal processor 30 might include an analog-to-digital converter connected to a personal computer running appropriate data collection and/or processing software. Signal processor 30 can average the output signal of each sensor in an array to obtain a real-time map of root-mean-squared (RMS) strain on a surface in response to steady state harmonic or stationary random disturbances. This data can be displayed on a display 32. The sensor array signals can also be processed by a dynamic data acquisition system to capture strain time histories. The resonant frequencies, damping and strain maps can be identified from captured transient time domain responses using the Eigensystem Realization Algorithm, a description of which is included in Juang, J. N. and Pappa, R. S., "An Eigensystem Realization Algorithm for Modal Parameter Identification and Model Reduction," *Journal of Guidance and Control Dynamics*, Vol. 8, No. 5, pp. 620–627, 1985.

The disclosed system for determining the dynamic response of physical structures successfully demonstrates the advantages of using piezoelectric polymer films to make a piezoelectric transducer array for that purpose. Although the disclosed invention is specialized, its teachings will find application in other areas where the cost and effort of data collection of a physical parameter is cost and effort prohibitive using presently available data sensors.

It is understood that modifications to the invention may be made, as might occur to one with skill in the field of this invention, within the scope of the appended claim. Therefore, all embodiments contemplated have not been shown in complete detail. Other embodiments may be developed without departing from the spirit of this invention of from the scope of the appended claim.

We claim:

1. A system for determining the dynamic response of a physical structure, comprising:

(a) a sheet of piezoelectric polymer film, the sheet having a first side and a second side;

(b) a contiguous first layer of conductive film on the first side of the sheet forming a first electrode;

(c) a non-contiguous second layer of conductive film on the second side of the sheet, the non-contiguous areas of the second layer forming an array of discrete second electrodes defining a corresponding array of discrete piezoelectric transducers;

(d) a plurality of sensor leads, each sensor lead connected in parallel with the other sensor leads to a single corresponding second electrode, wherein each single corresponding second electrode is connected to only one sensor lead; and, (e) a signal processor for receiving and processing electrical signals received from the array of discrete piezoelectric transducers, the signal processor including associated software for determining from the processed electrical signals relative strain amplitudes of the surface area of a physical structure onto which the sheet is attached.

2. The system for determining the dynamic response of a physical structure according to claim 1, further comprising an adhesive backing layer on the first electrode.

3. A method for determining the dynamic response of a physical structure, comprising the steps of:

(a) bonding to a surface of the physical structure a piezoelectric strain sensor array, the strain sensor array including:

(i) a sheet of piezoelectric polymer film, the sheet having a first side and a second side;

(ii) a contiguous first layer of conductive film on the first side of the sheet forming a first electrode;

(iii) a non-contiguous second layer of conductive film on the second side of the sheet, the non-contiguous areas of the second layer forming an array of discrete second electrodes defining a corresponding array of discrete piezoelectric transducers, and, (iv) a plurality of sensor leads, each sensor lead connected in parallel with the other sensor leads to a single corresponding second electrode, wherein each single corresponding second electrode is connected to only one sensor lead; and, (b) connecting the sensor leads to a signal processor for receiving and processing electrical signals received from the array of discrete piezoelectric transducers, the signal processor including associated software for determining from the processed electrical signals relative strain amplitudes of a surface area of the physical structure onto which the sheet is attached.

* * * * *